United States Patent [19]

Chiba

[11] Patent Number: 4,697,751

[45] Date of Patent: Oct. 6, 1987

[54] ULTRASONIC DISINTEGRATING APPARATUS

[76] Inventor: Sigeru Chiba, 1-8-9 Inamuragasaki, Kanagawa prefecture, Japan

[21] Appl. No.: 695,455

[22] PCT Filed: Dec. 5, 1983

[86] PCT No.: PCT/JP83/00427
§ 371 Date: Jan. 7, 1985
§ 102(e) Date: Jan. 7, 1985

[87] PCT Pub. No.: WO84/02350
PCT Pub. Date: Jun. 21, 1984

[30] Foreign Application Priority Data

Dec. 6, 1982 [JP] Japan ............... 57-184536[U]

[51] Int. Cl.⁴ ..................... B02C 19/18
[52] U.S. Cl. ..................... 241/301; 241/1; 241/2
[58] Field of Search ............... 241/1, 301, 2

[56] References Cited

U.S. PATENT DOCUMENTS 2,738,172 3/1956 Spiess et al. ............ 241/1 X

FOREIGN PATENT DOCUMENTS 55756 4/1983 Japan ............... 241/1

Primary Examiner—Mark Rosenbaum
Attorney, Agent, or Firm—Cushman, Darby & Cushman

[57] ABSTRACT

An ultrasonic disintegrating apparatus with a tank containing a liquid, an ultrasonic wave generating device operatively coupled to a bottom wall of the tank, and at least one vessel vertically immersed in the liquid contained in the tank such that ultrasonic waves propagated from the bottom wall of the tank disintegrate cells in the vessels. Each vessel includes a cylindrical metallic tube having an open upper end and a closed lower end, a cap detachably coupled to the open end of the tube, and a downwardly depending metallic bar suspended from the center of the cap into the metallic tube so as to terminate at a point spaced from the lower end of the metallic tube to thereby facilitate complete disintegration of cells within the vessel when exposed to ultrasonic waves.

1 Claim, 3 Drawing Figures

ULTRASONIC DISINTEGRATING APPARATUS

DESCRIPTION

1. Technical Field

The present invention relates to an ultrasonic disintegrating apparatus and, more particularly, to an ultrasonic disintegrating apparatus for use in separating small organs from cells, featuring a special vessel containing the solution of the cells to be disintegrated.

2. Background Art

In recent years, in the fields of clinical inspection, genetic engineering and so forth, it is often conducted to separate small organs from the cells by breaking the cell membrane, in order to investigate chemical compositions and biological properties of the small organs in the cell. For instance, in the field of clinical inspection, it is often attempted to disintegrate the cell for the purpose of biochemical analysis of the fluids in hematid or white blood cell. To this end, hitherto, ultrasonic disintegrating apparatus has been used for disintegrating the cell by ultrasonic waves. The conventional ultrasonic apparatus includes an oscillator, a vibrator and a horn or a tip. In use, the horn or tip is inserted from the upper side into a beaker or a test tube accommodating a solution containing hematid centrifugally separated from the blood and is immersed in the solution. The vibrator is excited by the output of the oscillator to impart an ultrasonic vibration to the hematid in the blood to cause a cavitation thereby to disintegrate the cell membranes of hematids or the like. In this conventional apparatus, a large quantity of the objects to be disintegrated, such as cells, are placed in a vessel and are uniformly vibrated by the horn, so that it is possible to disintegrate a large quantity of cells at a time. On the other hand, this conventional apparatus suffers from the following disadvantage. Namely, since the horn is kept inserted into the vessel, the inlet of the vessel has to be kept opened, i.e. the inside of the vessel is not sealed. When a noxious object is treated, therefore, the object is changed into aerosol by the application of the ultrasonic wave and is scattered widely. This is quite inconvenient for the inspectors and researchers. In addition, the object to be disintegrated is liable to be contaminated by external bacteria and microorganisms. Consequently, the small organs of the disintegrated cells cannot be held in the pure state and the quality of the research may be impaired so as to fail to meet the object of the research. Furthermore, the opened vessel tends to allow the leakage of the water content to cause a change in the pH value to failing to meet the expected result of disintegration. For instance, in the biochemical analysis of the hematids and white blood cells in the clinical inspection, it is necessary to avoid as much as possible the leak of water and change of the pH value. Unfortunately, however, the conventional apparatus could not adequately satisfy this demand. In a technique called "cell fractionation", the fluid produced as a result of breaking of the cells, i.e. the solution suspending the small organs in the cells, is subjected to a centrifugal separation so as to separate the small organs from one another. Since the conventional disintegrating method employs an open vessel, the fluid has to be poured into different vessels before subjected to the centrifugal separation. Consequently, the efficiency of the work is impaired disadvantageously. The temperature of the fluid filling the vessel is a factor which largely affects the propagation of the ultrasonic vibration and also the change of the object to be disintegrated, such as the cells. It is, therefore, necessary to conduct a suitable temperature control. In the case of conventional apparatus, the temperature control is conducted by cooling the fluid from the outside of the vessel, so that the control and management of the temperature are extremely difficult to conduct.

The propagation of the ultrasonic vibration, for instance, becomes higher as the fluid temperature gets lower. In addition, since the object to be disintegrated is usually stored at a low temperature, the expected disintegration result will be failed due to a thermal change because the object is heated up to a temperature considerably higher than the storage temperature during the disintegration. In this case, therefore, it is necessary to continuously cool the fluid. In the conventional disintegrating apparatus, however, it has not been possible to effect the cooling ideally, because the cooling is made from the external side of the vessel.

It is also to be pointed out that the conventional disintegrating apparatus not suited to the disintegration of various objects, although it is suitable for use in the disintegration of a large quantity of the same kind of object at a time.

The present invention has been accomplished under these circumstances. Namely, it is a primary object of the invention to make it possible to seal the cells while the cells are being disintegrated, thereby to ensure and safety of the researchers and operators and to protect the small organs produced as a result of the disintegration from being contaminated by external bacteria and microorganisms, while diminisning as much as possible the change of quality of the cells during disintegration. It is also an object of the invention to make it possible to directly control the temperature of the fluid in the vessel in which the ultrasonic vibration is propagated, thereby to facilitate the management of the fluid temperature which largely affects the propagation of the ultrasonic vibration. Still another object is to attain a high efficiency of disintegration of the cells. A further object of the invention is t provide a vessel which permits a direct centrifugal separation in a cell fractionation immediately after the disintegration of the cells, without requiring pouring of the disintegrated object into different vessels, thereby to attain a high efficiency of the work.

DISCLOSURE OF THE INVENTION

According to the invention, there is provided an ultrasonic disintegrating apparatus having a vessel containing a solution of cells to be disintegrated, the vessel being vertically immersed in a liquid contained by a tank, the tank having a bottom from which the ultrasonic wave is propagated to disintegrate the cells in the vessel, wherein the improvement comprises that the vessel includes a cylindrical metallic tube, a cap including a portion for closely fitting the inner peripheral surface of the metallic tube and an "O" ring fitted on the outer periphery of the portion of the cap, the cap being thereby detachably attached to the opening of the tube and a metallic bar suspended from the center of the cap into the metallic tube so as t leave a small clearance between the end of the metallic bar and the bottom of the tube.

According to this arrangement, it is possible to keep the cells in a sealed condition during the disintegration thereby to ensure the safety of the work while preventing the contamination of the small organs of disintegrated cells by external substances and minimizing the change of the cells during disintegration. In addition, since the fluid temperature in the tank from which the ultrasonic vibration is propagated can be controlled directly, it is possible to obtain a higher ultrasonic propagation effect. Furthermore, it is possible to conduct a small-lot large-variety disintegration at a high efficiency. In addition, since the vessel is constituted by a metallic tube having a cap firmly secured thereto by press-fitting or screwing, the vessel will never be broken even if it is dropped and, hence, will stand a long use. Furthermore, the fluid produced as a result of the disintegration can be subjected directly to the centrifugal separation for cell fractionation, thereby to afford a high efficiency of the work.

BRIEF DESCRIPTION OF THE DRAWINGS

The accompanying drawings show an embodiment of the invention in which.

BEST MODE FOR CARRYING OUT THE INVENTION

The invention will be more fully described hereinunder with reference to the accompanying drawings.

Figure 1:
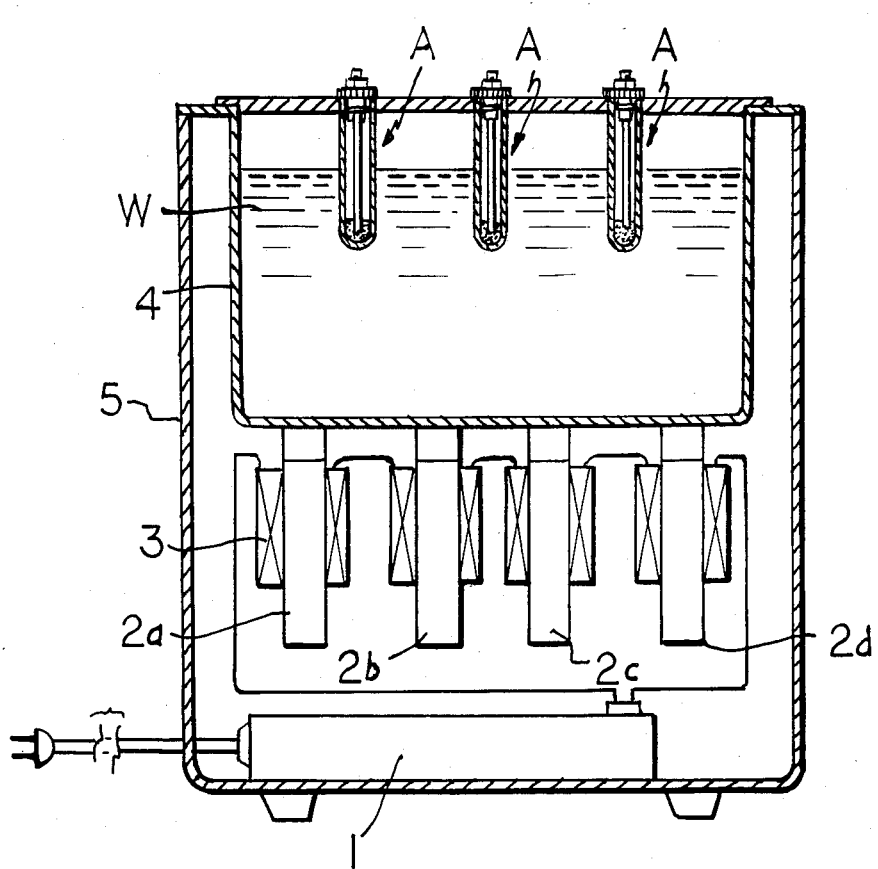
FIG. 1 is a vertical sectional side elevational view of the apparatus.
Figure 2:
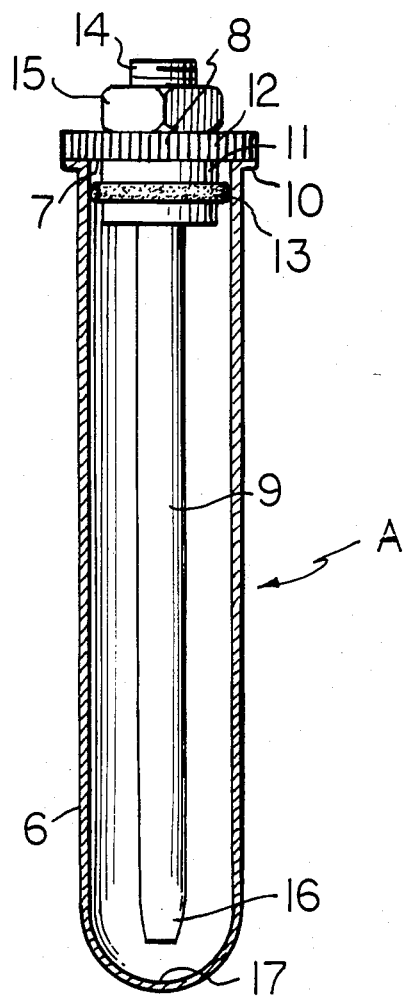
FIG. 2 is a sectional view of a first embodiment of a vessel.

A reference numeral 1 denotes a high-frequency wave oscillator, 2a to 2d denote ferrite magnetostriction vibrators mounting oscillator coils 3 adapted to be driven by the high-frequency wave oscillator 1, and 4 denotes a tank filled with a liquid W. These constituents constitute an ultrasonic cell disintegrating apparatus encased by a case 5. The invention is concerned with the vessel A for use in the ultrasonic cell disintegrating apparatus of the type described. A first embodiment of the vessel will be explained with specific reference to FIG. 2. The vessel A has a bottom-equipped cylindrical metallic tube 6, a cap hermetically closing open end 7 of the metallic tube 6, and a metallic bar 9 supported by the center of the cap 8. More specifically, the metallic tube 6 is made of stainless steel and the brim of the opening 7 is bent outwardly to form a flange 10. The cap 8 has a reduced-duameter portion 11 received in the opening 7 of the metallic tube 6 and an increased-diameter portion 11 seated on the flange 10 around the opening 7. An "O" ring 13 is fitted around the reduced-diameter portion 11. Thus, the opening 7 of the metallic tube 6 is hermetically sealed by both of the "O" ring 13 on the reduced-diameter portion 11 and the increased-diameter portion 12 seated on the flange 10. The metallic bar 9 is secured to the cap 8 in the following manner. Namely, the metallic bar 9 is inserted into the central hole formed in the cap 8 and a nut 15 is screwed to a female screw 14 formed on the upper portion of the metallic bar 9, so that the metallic bar 9 is fastened to and suspended from the cap 8 by screwing the nut 15.

A description will be made hereinunder as to how the vessel A having this construction is used. First of all, the cap 8 is detached and the solution T containing the cells to be disintegrated is charged into the metallic tube 6. Then, the cap 8 is attached to the metallic tube 6 with its reduced-diameter portion 11 press-fitted into the opening 7 while the increased-diameter portion 12 is seated on the flange 10. Consequently, the interior of the metallic tube 6 is hermetically sealed by the "O" ring 13 tightly contacting the inner peripheral surface of the metallic tube 6 and the bottom surface of the large-diameter portion 12 seated on the flange 10. As a result of the mounting of the cap 8, the metallic bar 9 is suspended such that a slight gap is left between the end 16 of the metallic bar 9 and the bottom 17. Thus, the end 16 is disposed in the solution in which the cells are dissolved.

A plurality of vessels A thus prepared are set in mounting holes 19 formed in a mounting plate 18 covering the tank 4. Consequently, the vessels A are immersed vertically in the liquid W filling the tank 4. Subsequently, the oscillator 1 is started to energize the exciting coils 3 thereby to vibrate the magnetostriction vibrators 2a to 2d so that the ultrasonic wave is radiated from the radiation surface. The ultrasonic vibration thus radiated is propagated through the liquid W and is transmitted to the vessels A to disintegrate the cell membranes of the cells. The disintegration mechanism is as follows. Namely, a disintegration effect is produced by the sound pressure of the ultrasonic vibration propagated through the liquid W and transmitted to the cells in the vessels A. Another disintegration effect is produced by selecting the length, thickness and the shape of the vessel A such that the vessel A makes a resonant vibration in response to the ultrasonic vibration. By so doing, the vessel as a whole makes a resonant vibration when it is subjected to the ultrasonic vibration. Namely, the metallic tube 6, cap 8 and the metallic bar 7 make a resonant vibration so that the end 16 of the metallic bar 9 imparts the ultrasonic vibration to the cells thereby to cause a cavitation in the solution dissolving the cells. This cavitation produces instantaneous and alternating pressure reduction and compression to disintegrate the cell membranes of the cells.

Examples of the disintegration experiment are shown below by way of reference.

Experiment 1

(1) Title of experiment

Number of live colibacillus and disintegration treating time (2) Outline

To measure how the of number of live colibacillus is decreased in relation to time as a result of the disintegration.

(3) Method

Live colibacillus (incubated in gelatin) was suspended in PBS which in turn was charged in a vessel and subjected to the disintegrating operation. Then, the PBS was suitably diluted by sterility PBS and a predetermined amount of diluted PBS was applied to a selective medium for colibacillus. After a one-day incubation at 37° C., the number of the live colibacillus in the starting solution was calculated from the number of colonies on the petri dish. The disintegrating treatment was conducted using an apparatus having an ultrasonic frequency of 19 KHZ and output power of 110 W, with a power supply of 50/60 HZ and 100 V voltage, keeping the liquid in the tank at 6° C.

(4) Result

| Time (min) | 0 | 0.62 | 1 | 2 | 3 |
|---|---|---|---|---|---|
| Number of live colibacillus | $3.96 \times 10^7$ | $1.81 \times 10^7$ | $1.38 \times 10^7$ | $4.92 \times 10^6$ | $1.62 \times 10^6$ |

-continued

| Time (min) | 0 | 0.62 | 1 | 2 | 3 |
|---|---|---|---|---|---|
| Disintegration rate (x) | 0 | 54.3 | 65.2 | 87.6 | 95.9 |

(5) Evaluation

It was confirmed that the number of live colibacillus (couple number) is decreased substantially linearly in relation to time.

Experiment 2

(1) Title of experiment

Yield of colibacillus DNA and disintegration time (2) Outline

To measure the rate of discharge of DNA of colibacillus out of the latter by the disintegrating treatment in relation to time.

(3) Method

A solution suspending colibacillus was disintegrated for a predetermined time length and was then subjected to a super centrifugal separation. Then, the amount of DNA of the supernate was measured by Burton method which makes use of coloring by diphenylamine, and the results were compared in relation to time.

(4) Results

| Experiment 1 | | | | |
|---|---|---|---|---|
| Time (min) | 0 | 10 | 25 | 40 |
| DNA amount (ug/ml) | 28 | 354.4 | 394.4 | 396 |
| Experiment 2 | | | | |
| Time (min) | 0 | 10 | 25 | 40 |
| DNA amount (ug/ml) | 70 | 548 | 545 | 553 |
| Experiment 3 | | | | |
| Time (min) | 0 | 2 | 5 | 7 |
| DNA amount (ug/ml) | 85 | 530 | 545 | 570 |

(5) Evaluation

Experiments (1) and (2) were conducted with long scale but no difference could be found between the state after 10 minutes and the state after 40 minutes. In the experiment (3), therefore, the change within 10 minutes was observed, but no substantial difference was found between the state after 2 minutes and the state after 7 minutes. This means that the colibacillus is disintegrated within 2 minutes to allow the internal DNA to be discharged.

Throughout the disintegrating process, the cells are hermetically sealed in the closed vessel A so that it is never changed into aerosol nor scattered to the outside. Therefore, the researchers and inspectors are safely protected even when the processed cells are noxious. In addition, the small organs of the disintegrated cells are prevented from being contaminated by external substances, and the leakage of water and, hence, a change in pH value attributable to the leakage of water are avoided to provide the disintegration result as expected.

Furthermore, since the cells are sealed in the vessels A, the liquid W in the tank 4 can be cooled directly. Namely, if it is necessary to lower the liquid temperature, cooling medium such as cooling water of the low temperature is directly put into the tank to directly adjust the liquid temperature. Since the liquid temperature can be adjusted easily by the described manner, it is possible to easily adjust the temperature of the liquid or to enhance the propagation of the ultrasonic vibration, thereby to minimize the thermal change of the quality of the cells. In addition, since a plurality of vessels A, each having a small size, can be set in the tank at a time, it is possible to disintegrate a plurality of kinds of cells at a high efficiency in a shorter period of time. It is also possible to subject the suspension liquid of the small organs to the centrifugal separation immediately after the disintegration of the cells, so that the separation of the small organs can be made at a high efficiency.

Figure 3:
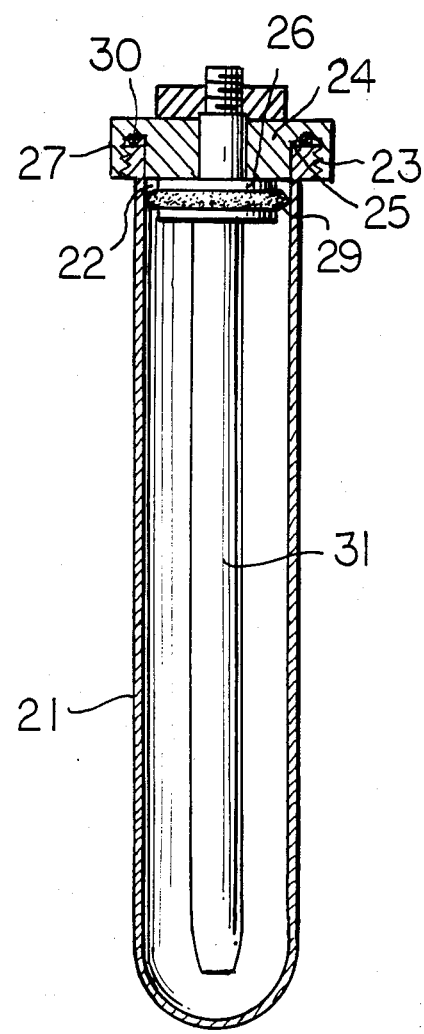
FIG. 3 is a sectional view of a second embodiment of the vessel.

Another example of the vessel will be described in detail with reference to FIG. 3. In this case, a female screw 23 is formed on the outer peripheral surface of the opening 22 of a bottom-equipped cylindrical metallic tube 21. On the other hand, a cap 24 is provided with an annular groove 25. The portion 26 of the cap inside of the annular groove 25 constitutes a portion which is received in the opening 22, while the portion 27 outside the groove 25 is provided with a male screw 28. An "O" ring 29 is fitted around the lower portion of the inner portion 26, while another "O" ring 30 is fitted to the bottom of the groove 25. A reference numeral 31 designates a metallic bar.

According to this arrangement, for filling the metallic tube 21 with a solution dissolving the cells, the cap 24 is rotated and removed and, after charging the solution into the metallic tube 21, the male screw thread 28 of the cap 24 is screwed to the female screw thread 23 on the cap 21, so that the cap 24 is firmly secured to the opening 22. It is thus possible to hermetically seal the inside of the metallic tube 21, so that function and advantages same as those produced by the first example can be brought about by this second example.

What is claimed is:

1. An ultrasonic disintegrating apparatus comprising:
a tank adapted for containing a liquid;
ultrasonic wave generating means operatively coupled to a bottom wall of said tank;
at least one vessel adapted for containing a solution of cells to be disintegrated, each said vessel being vertically immersed in liquid in said tank such that ultrasonic waves propagated from said bottom wall disintegrate said cells in each said vessel, each said vessel including a cylindrical metallic tube, said tube having an open upper end and a closed lower end for receiving said cells, a cap including a portion adapted to extend inwardly of said metallic tube and having an O-ring mounted on the outer periphery thereof so as to closely engage the inner peripheral surface of said metallic tube whereby said cap is detachably mounted to the upper end of said tube, and a metallic bar coupled at one end thereof to said cap and suspended therefrom such that the other end of said metallic bar terminates at a point spaced from the lower end of said metallic tube for facilitating the disintegration of material within said tube.

* * * * *